(12) United States Patent
Gscheidner et al.

(10) Patent No.: US 6,693,208 B2
(45) Date of Patent: Feb. 17, 2004

(54) COMPOUNDS AND COMPOSITIONS FOR DELIVERING ACTIVE AGENTS

(75) Inventors: David Gscheidner, Stamford, CT (US); Andrea Leone-Bay, Ridgefield, CT (US); Eric Wang, Ellicott City, MD (US); John J. Freeman, Fairfield, CT (US); Doris C. O'Toole, Carmel, NY (US); Lynn Shields, Port Chester, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 17 days.

(21) Appl. No.: 10/168,275

(22) PCT Filed: Dec. 18, 2000

(86) PCT No.: PCT/US00/34329

§ 371 (c)(1),
(2), (4) Date: Jul. 16, 2002

(87) PCT Pub. No.: WO01/44199

PCT Pub. Date: Jun. 21, 2001

(65) Prior Publication Data

US 2003/0216589 A1 Nov. 20, 2003

Related U.S. Application Data

(60) Provisional application No. 60/171,213, filed on Dec. 16, 1999.

(51) Int. Cl.$^7$ ............................................... C07C 23/00
(52) U.S. Cl. .................. 554/1; 554/36; 554/61; 554/62; 554/63; 554/65; 554/67; 564/152; 564/155; 564/161; 564/170; 564/171; 564/174; 424/451; 424/452; 424/464; 424/465; 424/485; 514/613; 514/616; 514/617; 514/621; 514/866; 514/889
(58) Field of Search ............................. 554/36, 6, 62, 554/63, 65, 67; 564/152, 155, 161, 170, 171, 174; 424/451, 452, 464, 465, 489; 514/613, 616, 617, 621, 866, 889

(56) References Cited

U.S. PATENT DOCUMENTS

| | | | |
|---|---|---|---|
| 3,795,739 A | 3/1974 | Birkmayer et al. | 424/274 |
| 3,939,253 A | 2/1976 | Bodor et al. | 424/309 |
| 4,035,507 A | 7/1977 | Bodor et al. | 424/311 |
| 4,061,466 A | 12/1977 | Sjoholm et al. | 424/311 |
| 4,147,767 A | 4/1979 | Yapel | 424/22 |
| 4,207,341 A | 6/1980 | Hubner et al. | 514/563 |
| 4,221,815 A | 9/1980 | Weyer et al. | 514/562 |
| 4,238,506 A | 12/1980 | Stach et al. | 424/319 |
| 4,239,754 A | 12/1980 | Stach et al. | 424/183 |
| 4,393,192 A | 7/1983 | Curatolo et al. | 528/292 |
| 4,442,090 A | 4/1984 | Kakeya et al. | 424/178 |
| 4,462,991 A | 7/1984 | Higuchi et al. | 424/177 |
| 4,499,299 A | 2/1985 | Bernstein et al. | 514/570 |
| 4,654,327 A | 3/1987 | Teng | 514/56 |
| 4,656,161 A | 4/1987 | Herr et al. | 514/56 |
| 4,692,433 A | 9/1987 | Hostetler et al. | 514/12 |
| 4,757,066 A | 7/1988 | Shiokari et al. | 514/210 |
| 4,835,312 A | 5/1989 | Itoh et al. | 564/205 |
| 4,873,087 A | 10/1989 | Morishita et al. | 424/433 |
| 4,878,942 A | 11/1989 | Motegi et al. | 71/109 |
| 4,900,730 A | 2/1990 | Miyauchi | 514/12 |
| 4,927,928 A | 5/1990 | Shroot et al. | 544/154 |
| 5,066,487 A | 11/1991 | Morelle et al. | 424/68 |
| 5,352,461 A | 10/1994 | Feldstein et al. | 424/493 |
| 5,447,728 A | 9/1995 | Milstein et al. | 424/490 |
| 5,451,410 A | 9/1995 | Milstein et al. | 424/490 |
| 5,629,020 A | 5/1997 | Leone-Bay et al. | 424/489 |
| 5,643,957 A | 7/1997 | Leone-Bay et al. | 514/563 |
| 5,650,386 A | 7/1997 | Leone-Bay et al. | 514/2 |
| 5,665,700 A | 9/1997 | Cho et al. | 514/2 |
| 5,705,529 A | 1/1998 | Matyus et al. | 514/541 |
| 5,709,861 A | 1/1998 | Santiago et al. | 424/184.1 |
| 5,714,167 A | 2/1998 | Milstein et al. | 424/490 |
| 5,750,147 A | 5/1998 | Kantor | 424/491 |
| 5,766,633 A | 6/1998 | Milstein et al. | 424/489 |
| 5,773,647 A | 6/1998 | Leone-Bay et al. | 562/444 |
| RE35,862 E | 7/1998 | Steiner et al. | 424/455 |
| 5,776,888 A | 7/1998 | Leone-Bay et al. | 514/2 |

(List continued on next page.)

FOREIGN PATENT DOCUMENTS

| | | |
|---|---|---|
| EP | 0036145 | 9/1981 |
| EP | 226223 | 6/1987 |
| EP | 0365183 | 10/1989 |
| EP | 0517211 | 9/1992 |
| EP | 0576941 | 6/1993 |
| ES | 369853 | 7/1971 |
| GB | 2095994 | 10/1982 |
| JP | 2239980 | 9/1990 |
| WO | 9747270 | 12/1997 |
| WO | 8807378 | 10/1998 |

OTHER PUBLICATIONS

Picciola G.: "Sintesi Di Acidi Chizaolinioici E Benzossazi-nonici E Studio Delle Loro Proprieta Antiniammatorie" IT, Societa Chimica Italiana Pavia vol. 31, No. 9 pp. 655–664 and English Translation.
Chem Abs 73548–12–6 (Apr. 1991).
Chem Abs 70204–54–5 (Apr. 1991).
Chem Abs 184360–83–342 (1975) Solubility and disassociation constants of some alicyclic acids.
Chemical Abstract, vol. 99(23) Abst. No. 191473h (1983).
Riveria, Theresa M. et al. "Oral Delivery of Heparin in Combination with Sodium N–[8–2–hydroxybenzoyl)amino] caprylate: Pharmacological Considerations" Pharmaceutical Research vol. 14(12) 1830–1834 (1997).

(List continued on next page.)

Primary Examiner—Deborah D. Carr
(74) Attorney, Agent, or Firm—Darby & Darby

(57) ABSTRACT

Amino acid derivative as carrier compounds and compositions which are useful in the delivery of active agents are provided. The active agents can be a peptide, mucopolysaccharide, carbohydrate, or lipid. Methods of administration, including oral administration, and preparation are provided as well.

29 Claims, No Drawings

U.S. PATENT DOCUMENTS

| | | | |
|---|---|---|---|
| 5,792,451 A | 8/1998 | Sarubbi et al. | 424/85.4 |
| 5,804,688 A | 9/1998 | Leone-Bay et al. | 562/444 |
| 5,811,127 A | 9/1998 | Milstein et al. | 424/490 |
| 5,863,944 A | 1/1999 | Leone-Bay et al. | 514/559 |
| 5,866,536 A | 2/1999 | Leone-Bay et al. | 514/2 |
| 5,876,710 A | 3/1999 | Leone-Bay et al. | 424/85.1 |
| 5,879,681 A | 3/1999 | Leone-Bay et al. | 424/85.1 |
| 5,939,381 A | 8/1999 | Leone-Bay et al. | 514/2 |
| 5,958,457 A | 9/1999 | Santiago et al. | 424/490 |
| 5,965,121 A | 10/1999 | Leone-Bay et al. | 424/85.2 |
| 5,989,539 A | 11/1999 | Leone-Bay et al. | 424/85.2 |
| 5,990,166 A | 11/1999 | Leone-Bay et al. | 514/563 |
| 6,001,347 A | 12/1999 | Leone-Bay et al. | 424/85.1 |

OTHER PUBLICATIONS

Leone–Bay, A. et al. "The evolution of an oral heparin dosing solution" Drugs of the Future vol. 22(8) 885–891 (1997).

Brayden, D. et al. "Heparin Absorption across the intestin: Effects of Sodium N–[8–2hydroxybenzoyl) Amino] Caprylate in rat in situ intestinal instillations ind in Caco–2 monolayers" Pharmaceutical Research vol. 14(12) 1772–1779 (1997).

Leone–Bay, A. "Acylated non–alpha–amino acids as novle agents for the oral delivery of heparin sodium, USP" Journal of Controlled Release 50: 41–49 (1998).

Leone–Bay, A. "4–[4–(2–Hydroxybenzoyl) amino]phenyl––butyric Acid as Novel Oral Delivery Agent for Recombinant Human Growth Hormone"; Journal of Medicinal Chemistry vol. 39, No. 13 pp 2571–2578 (1996).

Leone–Bay, A. "N–Acylated alpha–amino acids as novel oral delivery agents for proteins" ; Journal of Medicinal Chemistry vol. 38, 4263–4269 (1995).

Leone–Bay, A. "N–Acylated alpha–amino acids as novel oral delivery agents for proteins" ; Journal of Medicinal Chemistry vol 38, 4257–4262 (1995).

Ho Koc–Kan; et al. "A Practical Synthesis of ω–aminoalkanoic acid derivatives form Cycloalkanones" Synthetic Communication, vol. 26, No. 14: 2641–2649 (1996).

Gurrieri and Siracusa: "Thermal Condensation of Some alpha–aminoacids with Phatalic Acid" Thermochimica Acta, 7 (1973) 231–239.

Amino Yusuke et al. Chem Pharm Bull 36 pp. 4426–4434 (1998).

Brown et al., *J. Med. Chem.* 27:79–81 (1984).

Johansen, Marianne, et al. "The Kinetics of decompn. Of various N–Mannich bases of salicylamide" Int. J. Pharm. (1980), 7(2): 119–27 (1980).

COMPOUNDS AND COMPOSITIONS FOR DELIVERING ACTIVE AGENTS

CROSS-REFERENCE TO RELATED APPLICATIONS

This application is a U.S. national phase application under 35 U.S.C. §371 based upon co-pending International Application No. PCT/US/0034329 filed Dec. 18, 2000, which claims the benefit of priority of U.S. Provisional Application Serial No. 60/171,213 filed Dec. 16, 1999. The entire disclosure of the prior applications are incorporated herein by reference. The international application was published in the English language on Jun. 21, 2001 under Publication No. WO 01/44199.

FIELD OF THE INVENTION

The present invention relates to compounds for delivering active agents, such as biologically or chemically active agents, to a target. These compounds are well suited for forming non-covalent mixtures with active agents for oral, intracolonic, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastro-intestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; 5,863,944 and 5,866,536.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formulas:

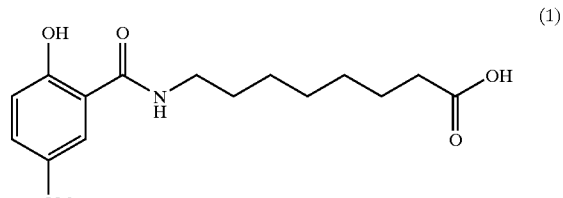

(1)

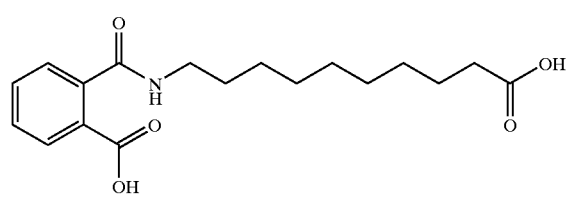

(2)

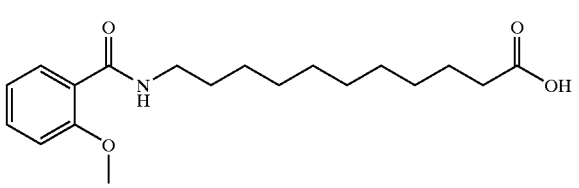

(3)

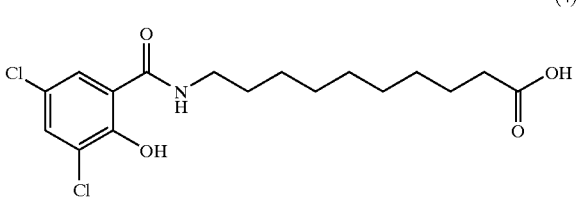

(4)

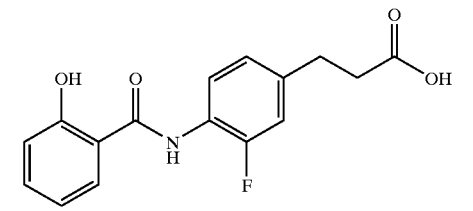
(5)

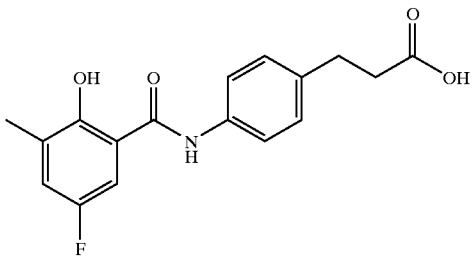
(6)

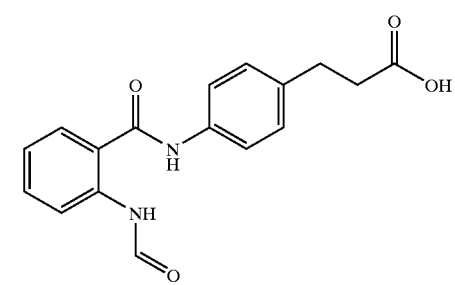
(7)

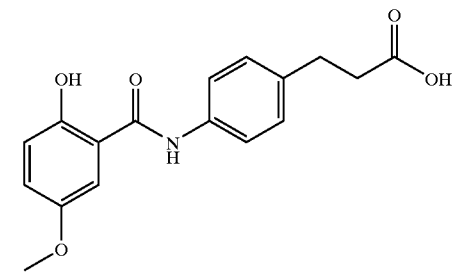
(8)

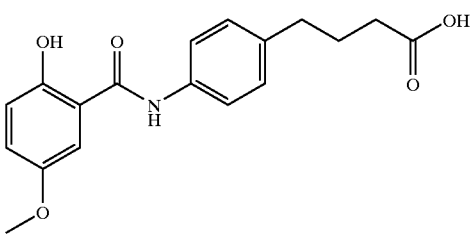
(9)

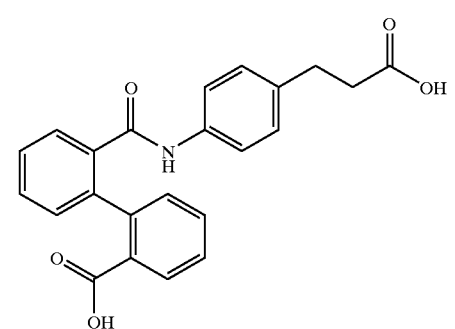
(10)

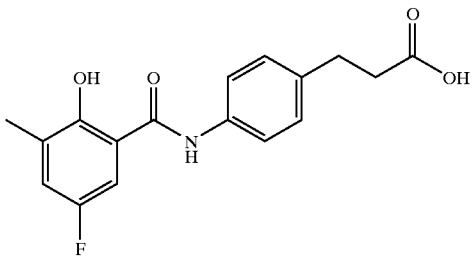
(11)

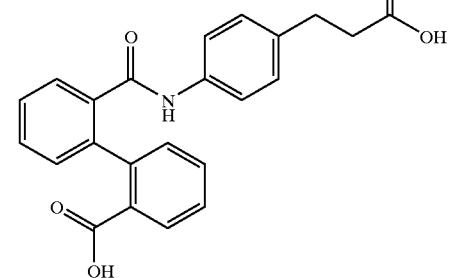
(12)

and salts thereof and mixture thereof.

The invention also provides a composition comprising at least one of the delivery agent compounds of the formulas listed above, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at least one of the delivery agent compounds listed above and the active agent to the animal. Preferred routes of administration include the oral and intracolonic routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formula above, and at least one active agent.

DETAILED DESCRIPTION OF THE INVENTION

Delivery Agent Compounds

The delivery agent compounds may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Salts of the delivery agent compounds of the present invention may be prepared by methods known in the art. For example, sodium salts may be prepared by dissolving the delivery agent compound in ethanol and adding aqueous sodium hydroxide.

In addition, poly amino acids and peptides comprising one or more of these compounds may be used.

An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The compounds described herein may be derived from amino acids and can be readily prepared from amino acids by methods within the skill of those in the art based upon the present disclosure and the methods described in WO96/30036, WO97/36480, U.S. Pat. No. 5,643,957 and 5,650,386. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0–500 mM sodium chloride gradient is employed.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of mucopolysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including $\alpha$, $\beta$ and $\gamma$; interleukins, including interleukin-1 and interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin; gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics (including gram-positive acting, bacteriocidal, lipopeptidal and cyclic peptidal antibiotics and daptomycin), anti-bacterials and anti-fungal agents; vitamins; analogs, fragments, mimetics or polyethylene glycol (PEG)-modified derivatives of these compounds; or any combination thereof.

Delivery systems

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
|---|---|
| Growth hormones | Growth disorders |
| Interferons | Viral infection; chronic cancer and multiple sclerosis |
| Interleukins. | Viral infection; cancer |
| Insulin, Insulin-like growth factor | Diabetes |
| Heparin. | Thrombosis; Prevention of blood coagulation |
| Calcitonin | Osteoporosis; Diseases of the bone |
| Erythropoietin | Anemia |
| Atrial naturetic factor | Vasodilation |
| Antigens | Infection |
| Monoclonal antibodies | Prevention of graft rejection; cancer |
| Somatostatin | Bleeding ulcer; Erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly, e.g. serum insulin levels.

DESCRIPTION OF THE PREFERRED EMBODIMENTS

The following examples illustrate the invention without limitation. All parts are given by weight unless otherwise indicated.

Proton nuclear magnetic resonance ($^1$H NMR) analyses for the compounds listed below were conducted on a 300 MHz Bruker spectrometer using dimethyl sulfoxide (DMSO-d$_6$) as the solvent unless otherwise indicated.

EXAMPLE 1

Compound Preparation

Preparation of Compound 1

5-methoxysalicylic acid (30.0 g, 0.1786 mol) and methylene chloride (350 ml) were placed in a 1 L round bottomed flask fitted with argon purge and magnetic stir bar. The resulting tan reaction mixture was cooled to 0° C. in an ice water bath. Triethylamine (39.68 g, 0.3929 mol) was added in one portion, followed by dropwise addition of acetyl chloride (15.42 g, 0.1964 mol) over a period of thirty-five minutes. The reaction mixture was allowed to come to room temperature overnight and then 350 mL of methylene chloride was added. The mixture was washed with two 300 ml portions of 0.5HCl, and then with two 300 ml portions of water. At this point it was noted that a tan solid had precipitated. This solid was isolated by filtration, recrystallized from methylene chloride and dried in vacuo. 26.24 g of 5-methoxyacetylsalicylic acid was isolated.

The above prepared 5-methoxyacetylsalicylic acid (26.24 g, 0.1250 mol) was placed in a 500 ml round bottomed flask fitted with Argon purge and magnetic stir bar. Methylene chloride (125 ml) and several drops of dimethylformamide were then added. A 60 ml addition funnel was placed atop the flask and thionyl chloride (22.30 g, 0.1874 mol) was added dropwise over a period of 25 minutes. The addition funnel was replaced with a condenser and the reaction mixture was heated at reflux for a period of approximately 1 hour. Heating was stopped and the reaction mixture allowed to cool to room temperature. Excess thionyl chloride and methylene chloride were removed under-vacuum yielding 29.00 g of 5-methoxyacetylsalicyloyl chloride.

A mixture of 8-aminocaprylic acid (23.89 g, 0.1503 mol) in methylene chloride (375 ml) was treated with chlorotrimethylsilane (32.76 g, 0.3005 mol) and was allowed to reflux for 90 minutes. The reaction mixture was cooled to 0° C. and then treated with triethylamine (22.76 g, 0.2254 mol). After this mixture stirred for approximately 5 min, a solution of 5-methoxyacetylsalicyloyl chloride (29.00 g, 0.1503 mol) in methylene chloride (50 ml) was added dropwise to the reaction mixture over a period of 35 minutes. The reaction mixture was allowed to stir for 30 minutes at 0° C. and then for 18 hrs at 25° C. Methylene chloride was removed in vacuo and 2N NaOH solution (200 ml) was added to the residue. This mixture was allowed to stir for 1 hour before the mixture was acidified to pH=1 with sulfuric acid solution (1N). The resulting mixture was extracted twice with 200 ml portions of ethyl acetate. The combined ethyl acetate layers were dried with sodium sulfate, and concentrated in vacuo. The resulting tan solid was recrystallized from a 1:1 ethanol:water solution to yield 30.70g of product as a white solid. Melting Point=96–99° C.

Preparation of Compound 2, Sodium Salt

Into a 3-necked, 250 mL round-bottom flask were measured 9.0 g (131 mmol) sodium nitrate, 15.0 g (14 mmol) of 10-bromodecyl phthalimide and 150 mL DMSO. The reaction mixture was stirred at room temperature for about 20 minutes, at which time 24.36 mL (426 mmol) of glacial acetic acid were added dropwise over 10 minutes. The reaction mixture was stirred and heated to 65° C. for about 2 hours, then cooled to room temperature and stirred overnight. The reaction mixture was poured into 200 mL of ethyl acetate. The organic phase was washed with two 100-mL portions of 0.5 N aqueous sulfuric acid, then was extracted with two 100 mL portions of 2 NaOH. The aqueous phase was cooled to 0° C., then acidified to pH=4 with 2N HCl. The resulting solids were collected by filtration, and recrystallized from ethanol:acetone:water (about 1:1:1)

Into a 500 mL Erlenmeyer flask was transferred 6.46 g (19.3 mmol) of the solid obtained above. The solid was dissolved in 120 mL of hot ethanol and the resulting solution was filtered through a celite pad. To the filtrate was added 2.27 mL of 8.5 N NaOH (19.6 mmol), and the resulting mixture was stirred for one hour. The reaction mixture was concentrated in vacuo to about half the original volume, diluted with 200 mL heptane, and the resulting solid was collected by filtration. This solid was transferred to a 500 mL Erlenmeyer flask, dissolved in 120 mL of hot ethanol, and the resulting solution filtered through a celite pad. To the filtrate was added 2.11 mL of 8.5 NaOH (18 mmol), and the resulting mixture was stirred for one hour. Hexanes were added and the resulting solids were collected by filtration, and dried in vacuo overnight to give 9.53 (91%) of the product as a sodium salt. Melting point: 180–200° C. Combustion analysis: %C: 56.06 (calc.), 55.84 (found); %H: 6.16 (calc.), 6.11 (found), %N: 3.63 (calc.), 3.49 (found) %Na: 11.94 calc.), 11.40 (found). $^1$H NMR Analysis: ($d_6$-DMSO): $\delta$11.1, t, 1H (NH); $\delta$7.7 dd, 1H (H ortho COONa); $\delta$7.38–7.18, m, 3H (remaining aromatic H); ü 3.16, q, 2H ($CH_2$ alpha to amide); ü1.89, t, 2H ($CH_2$ alpha to COONa); ü1.43, m, 4H ($CH_2$ beta to amide, $CH_2$ beta to COONa); ü1.43, m, 6H (remaining aliphatic $CH_2$).

Preparation of Compound 3

A slurry of 11-aminoundecanoic acid (5.00 g, 25 mmol) in methylene chloride (25 mL) was treated with chlorotrimethylsilane (6.35 mL, 5.43 g, 50 mmol) and was allowed to reflux for 90 minutes The reaction mixture was cooled to 0° C. and was then treated with triethylamine (5.23 mL, 3.79 g, 37.5 mmol). After this mixture stirred for about 5 min, a solution of o-anisoyl chloride (3.72 mL, 4.27 g, 25 mmol) in methylene chloride (10 mL) was added dropwise to the reaction mixture over a period of 15 minutes. The reaction mixture was allowed to stir for 30 minutes at 0° C. and then for 18 hrs at 25° C. Methylene chloride was removed in vacuo and 100 mL of saturated $NaHCO_3$ solution was added to the residue. This mixture was allowed to stir for 1 hr before the mixture was acidified to pH=1 with hydrochloric acid solution (1N). The resulting white solid was filtered off and dried in vacuo. The resulting white solid was washed in 1/1 ethyl acetate and water. The insolubles and concentrated ethyl acetate were combined and dried for 24 hour in vacuo at 25° C. Yield of product was 6.24 g (76.6%), melting point=88.5–91° C.

Preparation of Compound 4

Acetic anhydride (7.10 mL, 7.69 g, 75.0 mmol. 1.04 eq), 3,5-dichlorosalicylic acid (15.0 g, 72.5 mmol, 1.00 eq), and xylenes (40 mL) were added to a 250 mL, three-neck flask fitted with a magnetic stir bar, a thermometer, and a Dean-Stark trap with condenser. The flask was placed in a heating mantle, and heating of the cloudy white mixture begun. The reaction mixture became a clear solution around 100° C. Most of the volatile organics (xylenes and acetic acid) were distilled into the Dean-Start trap over three hours (135–146° C.). Distillation was continued for another hour (a total of 50 mL distilled), during which the pot temperature slowly rose to 165° C. and the distillate slowed to a trickle. The residue was poured off while still hot into an aluminum tray. Upon cooling a brittle yellow glass formed. The solid was ground to a fine powder. The oligo (3,5-dichlorosalicylate) produced was used without further purification.

A slurry of 3.0 g of (16.0 mmol, 1.1 eq) 10-aminodecanoic acid, 9 ml (18.0 mmol, 1.13 eq) of 2 N aqueous sodium hydroxide and 30 ml of dioxane was added to a white slurry of 3.97 g (20.8 mmol, 1.3 eq) of oligo (3,5-dichlorosalicylate) and 30 ml of dioxane in a 250 mL round bottom flask equipped with a magnetic stir bar and reflux condenser. The reaction mixture was heated to 90° C. for 20 hours (at which time no further change was observed, by HPLC). The reaction mixture was cooled to 25° C. and acidified to pH=1 with 2N aqueous hydrochloric acid. The mixture was concentrated in vacuo (60° C., 50 mm). The resulting solid was recrystallized twice from ethanol-water decolorized with charcoal but was not yet clean. Column chromatography using 5:1 hexanes/ethyl acetate-1% acetic acid as eluant gave one fraction as acid and another as ethyl ester. The ethyl ester was hydrolyzed to the acid using 4 ml of 2N aqueous sodium hydroxide and acidified with 2N aqueous hydrochloric acid. The acid was isolated by filtration. The combined acid portions were triturated with methylene chloride and hexanes to give 1.22 g of N-(3,5-dichlorosalicyloyl)-10-aminodecanoic acid.

Preparation of Compound 5, Sodium Salt

Sulfuric acid (14.5 mL) was slowly added to a solution of 3-fluoro-4-nitrotoluene (10.0 g, 64 mmol) in acetic acid (75 mL) at 5° C. Cromium trioxide (17.92 g, 180 mmol) was added slowly over 1 hour. The reaction was kept below 10° C. for an additional 2 hours and then poured into ice water (700 mL) and the resulting yellow solids filtered off. The solids were stirred in 2% $NaHCO_3$ for 15 minutes, filtered, dried in vacuo, then heated to reflux for 15 minutes in a solution of: water (60 mL), concentrated HCl (40 mL), and ethanol (11 mL). The yellow solids were isolated by filtration, 3.16 g 4-nitro-2-fluorobenzaldehyde (29.2% yield).

A suspension of 4-nitro-2-fluorobenzaldehyde (3.16 g, 18.7 mmol), malonic acid (2.14 g, 21 mmol) pyridine (catalytic) and ethanol (10 mL) was heated to reflux for 6 hours. The suspension became a clear solution upon heating. Upon cooling to room temperature solids formed and were isolated by filtration. The solids were washed with cool (15° C.) ethanol and then with 1N HCl and dried, giving 3.32 g 4-nitro-2-fluorocinnamic acid (90% yield).

4-nitro-2-fluorocinnamic acid (3.32 g, 17 mmol) was dissolved in ethyl acetate (50 mL) and ethanol (10 mL) in the reaction flask of a PAR reactor. Pd/C (100 mg) was added and the reactor charged with 100 psi hydrogen. The reactor was recharged to 100 psi after 3 hours and the reaction stirred overnight. The reaction mixture was filtered through a bed of celite and the product isolated in vacuo, 2.53 g 3-(4-amino-2-fluorophenyl)propionic acid (81.2%).

A slurry of 3-(4-amino-2-fluorophenyl)propionic acid (2.53 g, 13.8 mmol) in methylene chloride (100 mL) was treated with chlorotrimethylsilane (3.50 mL, 2.99 g, 27.6 mmol) and was allowed to reflux for 2.25 hours. The reaction mixture was cooled to 0° C. and was then treated with triethylamine (5.77 mL, 4.19 g, 41.4 mmol). After this mixture stirred for about 20 minutes, a solution of acetylsalicyloyl chloride (2.74 g, 13.8 mmol) in methylene chloride (20 mL) was added dropwise to the reaction mixture over a period of 15 minutes. The reaction mixture was allowed to stir for 1 hour at 0° C. and then for 18 hours at 25° C. Methylene chloride was removed in vacuo and 100 mL of NaOH solution (2N) was added to the residue and stirred for 1 hr before the mixture was acidified to pH=1 with concentrated hydrochloric acid solution. The resulting solid was recrystallized from a 1/1 ethanol/water mixture yielding a white solid, which was dried in vacuo at 25° C. yielding 1.88 g, 43.7%. The solids were dissolved in ethanol (10 mL) with warming. A solution of NaOH (0.25 g, NaOH in 0.75 mL water) was added to the warm ethanol solution. The volume was reduced by half in vacuo. The concentrate was stirred in heptane at 0° C. then concentrated in vacuo producing 1.8 g of sodium 3-(4-salicyloylamino-3-fluorophenyl)propionate as a tan solid (82% yield).

Preparation of Compound 6, Sodium Salt

A mixture of O-acetyl-(5-fluoro-3-methyl)salicylic acid (2.05 g, 9.8 mmol) and $SOCl_2$ (0.8 mL, 10.97 mmol) in 12 mL methylene chloride was allowed to reflux for 3 hours The reaction mixture was concentrated in vacuo, then dissolved in THF (10 mL). The acid chloride solution was then added dropwise to a cooled, stirred mixture of 3-(4-aminophenyl)propionic acid (1.63 g, 9.87 mmol) in THF (35 mL) and NaOH (0.81 g, 20.2 mmol) in $H_2O$ (16.2 mL). The resulting mixture was stirred at 0° C., then at room temperature for 18 hours. Aqueous NaOH solution (2.0 N, 20 mL) was added and the mixture stirred for 0.5 hour. The mixture was concentrated in vacuo and the resulting residue was acidified. The resulting precipitate was collected by filtration, washed generously with water, and recrystallized from methanol/acetone/$H_2O$. A light tan solid (free acid of the compound) was isolated (12.1 g, 68%), melting point 165–166° C.

A solution of the free acid derivative of the compound (2.1 g, 6.62 mmol) in ethanol (20 mL) was added dropwise to a solution of $NaHCO_3$, (0.59 g, 7.02 mmol) in $H_2O$ (5 mL). The mixture was stirred for 0.5 h, then concentrated in vacuo. The residue was dissolved in acetone. Ethyl acetate was added until the solution turned cloudy. The mixture was kept in the refrigerator overnight. Crystals formed and were filtered, and dried to yield 2.2 g (98%) of product as a sodium salt, melting point 240° C., with decomposition; $^1H$ NMR (DMSO) $\delta$2.05 (s, 3H), 2.46 (t, 2H), 2.76 (t, 2H), 6.86 (dd, 1H), 7.12 (d, 2H) 7.31 (dd, 1H) 7.58 (d, 2H)

Preparation of Compound 7, Sodium Salt

Into a 250 mL round-bottom flask were measured 10 g (61 mmol) isatoic anhydride, 10.1 g (61 mmol) of 3-(4-aminophenyl)propionic acid, 75 mL of 1,4-dioxane, and 15 mL water. The reaction mixture was stirred and heated to reflux for about seven hours, then cooled to room temperature and stirred overnight. The reaction mixture was cooled to 0° C., then diluted with 50 mL of water. The resulting solid was collected by filtration, dried overnight in a vacuum oven, and used as is in the next reaction.

Into a round-bottom flask was transferred 3.0 g (11 mmol) of the solid obtained above. This was cooled to 0° C. Separately, an acetic-formic anhydride complex was prepared in the following manner: acetic anhydride (1.0 mL) was cooled to 0° C. To this was added 0.5 mL of ice-cold formic acid. The resulting mixture was stirred at 0° C. for one hour, at which time methylene chloride was added. The cold acetic-formic anhydride complex was added to the cold solid obtained in the first reaction. The resulting mixture was stirred at 0° C. for 2–3 hours, then gradually warmed to room temperature and stirred for three days. 2 N HCl was added to the reaction mixture, which then formed a gummy solid. Ethyl acetate was then added, forming an emulsion which was filtered through a separatory funnel. Solids were isolated and recrystallized from ethanol:acetone:water (about 1:1:1) to give the free acid (melting point 200–204° C.).

Into a 250 mL Erlenmeyer flask was transferred 1.21 g (2.9 mmol) of the solid obtained above. The solid was dissolved in 100 mL of hot ethanol, and the resulting solution filtered through a celite pad. To the filtrate was added 0.47 mL of 8.5 N NaOH (4.0 mmol), and the resulting mixture was stirred for 30 minutes. The reaction mixture was concentrated in vacuo to about half the original volume, diluted with 30–50 mL heptane, and the resulting solid was collected by filtration. The solid was dried in vacuo-overnight to give 1.05 g (79%) of product as the sodium salt. Melting point: >260° C. (upper limit of instrument used). Combustion analysis: %C: 60.12 (calc.), 161.70 (found); %H: 4.85 (calc.), 4.64 (found); %N: 8.25 (calc.), 8.20 (found); %Na: 6.77 (calc.), 5.78 (found).

Preparation of Compound 8

A mixture of O-acetyl-5-methoxysalicylic acid (2.47 g, 12.5 mmol) and $SOCl_2$ (2.0 mL, 27.4 mmol) in 15 mL methylene chloride was allowed to reflux for 4 hours The reaction mixture was concentrated in vacuo, then dissolved in THF (15 mL). The acid chloride solution was then added dropwise to a cooled, stirred mixture of 3-(4-aminophenyl) propionic acid (2.06 g, 12.47 mmol) in THF (50 mL) and NaOH (1.03 gm 25.75 mmol) in $H_2O$ (20.0 mL). The resulting mixture was stirred at 0° C., then at room temperature for 18 hours. Aqueous NaOH solution (2.0 N, 20 mL) was added and the mixture stirred for 0.5 hour. The mixture was concentrated in vacuo and the resulting residue was acidified. The resulting precipitate was collected by filtration, washed generously with water, and recrystallized from methanol/acetone/$H_2O$ to yield the product as a pale yellow solid (2.0 g, 51%), melting point 216–218° C.

Preparation of Compound 9

A mixture of O-acetyl-5-methoxysalicylic acid (2.20 g, 11.10 mmol) and $SOCl_2$ (2.0 mL, 27.4 mmol) in 10 mL methylene chloride was allowed to reflux for 3 hours The reaction mixture was concentrated in vacuo, then dissolved in THF (10 mL). The acid chloride solution was then added dropwise to a cooled, stirred mixture of 4-(4-aminophenyl) butanoic acid (2.00 g, 11.16 mmol) in THF (50 mL) and NaOH (0.93 g, 23.25 mmol) in $H_2O$ (19.0 mL). The resulting mixture was stirred at 0° C., then at room temperature for 18 hours. Aqueous NaOH solution (2.0 N, 20 mL) was added and the mixture stirred for 0.5 hour. The mixture was concentrated in vacuo and the resulting residue was acidified. The resulting precipitate was collected by filtration, washed generously with water, and recrystallized from methanol/acetone/$H_2O$ to yield the product as an orange solid (2.3 g, 63%), melting point 189–190° C.

Preparation of Compound 10

To a slurry of 3.68 g (22.3 mmol) of 3-(4-aminophenyl) propionic acid in 30 mL of methylene chloride, was added 5.66 mL of chlorotrimethylsilane (44.6 mmol) dropwise via syringe. The reaction mixture was heated to reflux for about three hours, then cooled to 0° C. Triethylamine (9.32 mL. 66.9 mmol) was added dropwise to the cold reaction mixture, and stirred for about 15 minutes. A slurry of 5.0 g (22.3 mmol) of diphenic anhydride in 30 mL of methylene chloride was added dropwise to the cold reaction mixture. The reaction mixture was allowed to stir for 30 minutes at 0° C. and then overnight at room temperature. The organic phase was washed twice with 2 N HCl, once with water, and once with brine, then dried over sodium sulfate and concentrated in vacuo. The resulting off-white solid was recrystallized from methylene chloride-hexanes to give 1.61 g (18%) of the product. Melting point: 165–170° C. Combustion analysis: %C: 70.95 (calc.), 70.29 (found); %H: 4.88 (calc.). 4.99 (found); %N 3.59 (calc.), 3.51 (found); $^1$H NMR Analysis: (d$_6$-DMSO): δ12.5, s, 2H (COOH); δ9.85, t, 1H (NH); δ7.83–7.08 m, 12H (aromatic H); δ2.72, t, 2H ($CH_2$ alpha to COOH); ü 2.46, t, 2H ($CH_2$ beta to COOH).

Preparation of Compound 11

A slurry of 3-(4-aminophenyl)propionic acid (7.27 g, 44 mmol) in methylene chloride (100 mL) was treated with chlorotrimethylsilane (11.17 mL, 88mmol) and was allowed to reflux for 90 minutes The reaction mixture was cooled to 0° C. and was then treated with triethylamine (18.4 mL, 132 mmol). After this mixture was stirred for about 5 minutes a solution of 4-methoxy-2-acetylbenzoyl chloride (10.0 g, 44 mmol) in methylene chloride (20 Ml) was added dropwise to the reaction mixture over a period of 15 minutes. The reaction mixture was allowed to stir for 30 min at 0° and then for 18 hrs at 25° C. Methylene chloride was removed in vacuo and 100 mL 2N NaOH was added to the residue. This mixture was allowed to stir for 2 hr before the mixture was acidified to pH=1 with concentrated hydrochloric acid solution. The resulting solid was filtered off and dried in vacuo. The solids were recrystallized in 1/1 ethanol/water and in vacuo at 25° C. Yield of product was 8.51 g, 61.3%.

Preparation of Compound 12

A slurry of 4-chloro-3-nitrocinnamic acid (12.2 g, 53.2 mmol), ethyl alcohol (50 mL) and ethyl acetate (20 mL) was treated with 5% Platinum sulfide on carbon (0.6 g) and was placed in a Parr autoclave. The autoclave was placed under a hydrogen atmosphere and heated overnight at 50° C. After cooling to room temperature, the reaction mixture was filtered through celite, and was concentrated in vacuo to yield 10.6 g of 3-(4-chloro-3-aminophenyl)propionic acid.

A mixture of 3-(4-chloro-3-aminophenyl)propionic acid (4.85 g, 26.5 mmol) in methylene chloride (60 ml) was treated with chlorotrimethylsilane (5.75 g, 53.0 mmol) and was allowed to reflux for 90 minutes. The reaction mixture was cooled to 0° C. and then treated with triethylamine (8.04 g, 79.5 mmol). In a separate round bottomed flask, 4-methoxy-2-acetylsalicylic acid (13.91 g, 66.3 mmol), methylene chloride (50 ml) and several drops or dimethyl formamide were added. Oxalyl chloride (11.55 g, 132.5 mmol) was then added dropwise to this mixture. After the addition was completed, the mixture was allowed to stir for approximately 1 hr at room temperature before the solvent was removed in vacuo. The residue was then taken up in methylene chloride and added to the mixture in the first round, bottomed flask dropwise. This mixture was allowed to come to room temperature overnight. The reaction mixture was then extracted with two portions of 2N HCl solution, and was washed with one portion of water and with one portion of brine. The organic layer was dried over sodium sulfate and concentrated in vacuo, yielding a solid that was taken up in 2N NaOH solution. This mixture stirred for about 1 hr. before it was acidified with 49% $H_2SO_4$ solution and then cooled in an ice water bath. The resulting orange solids were isolated by filtration, and were recrystallized from a solution of ethyl acetate and hexane. The desired product was isolated in a yield of 3.54 g. melting point=195–200° C.

EXAMPLE 2

Salmon Calcitonin (sCT) Oral Delivery

Oral dosing (PO)compositions of delivery agent compound and salmon calcitonin (sCT) in water were prepared. Typically 450 mg of compound was added to 2.0 mL of water. Either the sodium salt of the compound was used or the free acid was converted to the sodium salt by stirring the resultant solution and adding one equivalent of sodium hydroxide(1.0 N) and diluting with water. The solution was vortexed, then heated (about 37° C.) and sonicated. The pH was adjusted to about 7 (6.5 to 8.5) with NaOH or HCL. 90 mg sCT from a stock solution was added to the solution. Water was then added to bring the total volume to about 3.0 mL (varies depending on solubility of the delivery agent compound). The final delivery agent compound dose, sCT dose and volume dose amounts are listed below in Table 1.

The typical dosing and sampling protocols were as follows. Male Sprague-Dawley rate weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger.

Blood samples were collected serially from the tail artery typically at time=0, 10, 20, 30, 60 and 90 minutes. Serum sCT was determined by testing with a EIA kit (Kit # EIAS-6003 from Peninsula Laboratories, Inc., San Carlos, Calif.) modifying the standard protocol from the kit as follows: incubated with 50 pl peptide antibody for 2 hours with shaking in the dark, washed the plate, added serum and biotinylated peptide and diluted with 4 mL buffer, and shook overnight in the dark. Numbers were adjusted according to baseline values obtained at time=0. The results from the five rats in each dosing group were averaged for each time point. The maximum is reported below in Table 1.

TABLE 1

Oral delivery of Salmon Calcitonin (sCT)

| Compound | Volume Dose (ml/kg) | Compound Dose (mg/kg) | sCT Dose (µg/kg) | Mean Peak Serum Sct (pg/ml ± SD) (SE) | AUC |
| --- | --- | --- | --- | --- | --- |
| 2 | 1 | 150 | 30 | 80 ± 75 (37) | 1777 |
| 2 | 1 | 150 | 30 | 132 ± 143 (64) | 4611 |
| 3 | 1 | 150 | 30 | 40 ± 38 (17) | n/a |
| 9 | 1 | 150 | 30 | 143 ± 121 (60) | 6775 |
| 9 | 1 | 150 | 30 | 15 ± 34 (15) | 0 |
| 10 | 1 | 150 | 30 | 213 ± 48 (24) | 10364 |
| 11 | 1 | 150 | 30 | 123 ± 141 (37) | n/a |
| 12 | 1 | 150 | 30 | 184 ± 179 | 1840 |
| 12 | 1 | 150 | 30 | 43.50 ± 60.54 | 0 | n/a — not available

Heparin Delivery Oral/Intracolonic Delivery

Oral gavage (PO) and/or intracolonic (IC) dosing solutions containing a delivery agent compound and heparin sodium USP in 25% aqueous propylene glycol were prepared. Either the sodium salt of the compound was used or the free acid was converted to the sodium salt with one equivalent of sodium hydroxide. Typically, delivery agent compound and heparin (about 166–182 IU/mg) were mixed by vortex as dry powders. This dry mixture was dissolved in 25% v/v aqueous propylene glycol, vortexed and placed in a sonicator (about 37° C.). The pH was adjusted to about 7 (6.5 to 8.5) with aqueous NaOH (2N). The dosing solution was sonicated to produce a clear solution. The final volume was adjusted to 3.0 mL. The final delivery agent compound dose, heparin dose and volume dose amounts are listed below in Table 2.

The typical dosing and sampling protocols were as follows. Male Sprague-Dawley rats weighing between 275–350 g were fasted for 24 hours and were anesthetized with ketamine hydrochloride (88 mg/kg) intramuscularly immediately prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm 8 fr Rusch catheter was adapted to a 1 ml syringe with a pipette tip. The dosing catheter was inserted into the colon through the anus. until the tube was no longer visible. The dosing solution was expressed slowly into the colon.

Citrated blood samples were collected by cardiac puncture following the administration of ketamine (88 mg/kg), typically at time—0.25, 0.5, 1.0 and 1.5 hours. Heparin activity was determined by utilizing the activated partial thromboplastin time (APTT) according to the method of Henry, J. B., Clinical Diagnosis and Management by Laboratory Methods, Philadelphia, Pa., W. B. Saunders (1979). Previous studied indicated baseline values of about 20 sec. Results from the five rats in each group were averaged for each time point. The maximum is reported below in Table 2.

TABLE 2

Oral/Intracolonic Delivery of Heparin

| Compound | Method of Administration | Volume Dose (ml/kg) | Compound Dose (mg/kg) | Heparin Dose (mg/kg) | Mean Peak APTT (sec) ± SD |
| --- | --- | --- | --- | --- | --- |
| 1 | PO | 3 | 200 | 100 | 65.5 ± 9.1 |
| 1 | PO | 3 | 200 | 100 | 58.2 ± 55.2 |
| 1 | IC | 1 | 50 | 25 | 102.3 ± 130.4 |
| 3 | IC | 1 | 50 | 25 | 44.2 ± 16.2 |
| 4 | IC | 1 | 50 | 25 | 94 ± 47.5 |
| 5 | PO | 3 | 200 | 100 | 32.6 ± 5 |
| 5 | IC | 1 | 50 | 25 | 89.9 ± 68.6 |
| 6 | PO | 3 | 200 | 100 | 33.8 ± 18.7 |
| 6 | IC | 1 | 50 | 25 | 90.6 ± 50.9 |
| 7 | IC | 1 | 50 | 25 | 28.6 ± 6.1 |
| 8 | IC | 1 | 50 | 100 | 266.4 ± 165.7 |
| 9 | IC | 1 | 50 | 100 | 192.8 ± 50.9 |

Recombinant Human Growth Hormone (rhGH) Oral/Intracolonic Delivery

Oral gavage (PO) and/or intracolonic (IC) dosing solutions of delivery agent compound and rhGH in phosphate buffer were prepared. A solution of the compound was made either with the sodium salt of the compound or by converting the free acid to its sodium salt. Typically, a solution of the compound was prepared in phosphate buffer and stirred, adding one equivalent of sodium hydroxide (1.0 N) when making sodium salt. The final dosing solutions were prepared by mixing the compound with an rhGH stock solution (15 mg rhGH/ml) and diluting to the desired volume (usually 3.0 ml). The compounds and rhGH dose amounts are listed below in Table 3.

The typical dosing and sampling protocols were as follows. Male Sprague-Dawley rats weighing between 200–250 g were fasted for 24 hours and administered ketamine(44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip avoiding contact with the eye of the tube, and the tube was inserted into the colon through the anus until the tube was no longer visible. The solution was injected by pressing the syringe plunger, and the-tube was removed.

Blood samples were collected serially from the tail artery, typically at time=0, 15, 30, 45, 60 and 90 minutes for oral and 0, 10, 20, 30, 60 and 90 for IC dosing. The five samples from each time period were pooled. Serum rHGH concentrations were quantified by an rHGH immunoassay test kit (Kit #K1F4015 from Genzyme Corporation Inc., Cambridge, Mass.). Previous studies indicated baseline values of about zero.

The maximum concentration for each group is reported below in Table 3.

TABLE 3

Oral/Intracolonic Delivery of rhGH in Rats

| Compound | Method of Administration | volume dose (ml/kg) | Compound Dose (mg/kg) | rHGH Dose (mg/kg) | Mean Peak Serum Sct (ng/ml) |
|---|---|---|---|---|---|
| 1 | PO | 1 | 200 | 3 | 19.4 |
| 2 | PO | 1 | 200 | 3 | 6.39 |
| 3 | PO | 1 | 200 | 3 | 0 |
| 11 | PO | 1 | 200 | 3 | 0 |
| 12 | PO | 1 | 200 | 3 | 189 |
| 12 | PO | 1 | 200 | 3 | 32.86 |
| 12 | PO | 1 | 200 | 3 | 15.13 |

Parathyroid Hormone Delivery (PTH 1–34) Oral/Intracolonic Delivery

Oral gavage (PO) and/or intracolonic (IC) dosing solutions of delivery agent compound and human parathyroid hormone residues 1–34 (PTH) in water were prepared. A solution of the compound was made either with the sodium salt of the compound or by converting the free acid to its sodium salt. Typically, a solution of the compound was prepared in water and stirred, adding one equivalent of sodium hydroxide (1.0 N) when making sodium salt. The final dosing solutions were prepared by mixing the compound with a PTH stock solution (typically having a concentration of 5 mg PTH/ml) and diluting to the desired volume (usually 3.0 ml). The final compound, PTH and volume dose amounts are listed below in Table 4.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing. A dosing group of five rats was administered one of the dosing solutions. For oral gavage (PO) dosing, an 11 cm Rusch 8 French catheter was adapted to a 1 mL syringe with a pipette tip. The syringe was filled with dosing solution by drawing the solution through the catheter, which was then wiped dry. The catheter was placed down the esophagus leaving 1 cm of tubing past the rat's incisors. Solution was administered by pressing the syringe plunger. For intracolonic (IC) dosing, a 7.5 cm Rusch catheter tube (French 8 or 6) was adapted to a syringe with an Eppendorf pipette tip. The syringe was filled with the dosing solution by drawing the solution through the catheter tube. The catheter tube was wiped dry. K-Y jelly was applied to the tip, avoiding contact with the eye of the tube, and the tube was inserted into the colon through the anus until the tube was no longer visible. The solution was injected by pressing the syringe plunger, and the tube was removed.

Blood samples were collected serially from the tail artery, typically at time=0, 15, 30, 45, 60 and 90 minutes for oral and 0, 10, 20, 30, 60 and 90 for IC dosing. Serum PTH concentrations were quantified by an PTH radioimmunoassay kit (Kit # RIK 6101 from Peninsula Laboratories, Inc. San Carlos, Calif.). Previous studies indicated baseline values of about zero. Results from the five rats in each group were averaged for each time point. The maximum is reported below in Table 4.

TABLE 4

Oral/Intracolonic Delivery of PTH in Rats

| Compound | Method of Administration | Volume Dose (ml/kg) | Compound Dose (mg/kg) | PTH Dose (mg/kg) | Mean Peak Serum [PTH] (pg/ml) ± SD |
|---|---|---|---|---|---|
| 1 | PO | 1 | 100 | 200 | 347 ± 377 |
| 1 | PO | 1 | 100 | 200 | 917 ± 175 |
| 1 | PO | 1 | 100 | 200 | 890 ± 1123 |
| 1 | PO | 1 | 100 | 200 | 484 ± 776 |
| 1 | PO | 1 | 100 | 200 | 2302 ± 1717 |
| 2 | PO | 1 | 100 | 200 | 40 ± 51 |
| 2 | PO | 1 | 100 | 200 | 441 ± 424 |
| 3 | PO | 1 | 100 | 200 | 0 |
| 3 | PO | 1 | 100 | 200 | 51 ± 122 |
| 4 | PO | 1 | 100 | 200 | 0 |
| 5 | PO | 1 | 100 | 200 | 246 ± 293 |
| 5 | PO | 1 | 100 | 200 | 588 ± 118 |
| 6 | PO | 1 | 100 | 200 | 183 ± 176 |
| 6 | PO | 1 | 100 | 200 | 464 ± 171 |
| 6 | PO | 1 | 100 | 200 | 1005 ± 630 |
| 6 | PO | 1 | 100 | 200 | 57 ± 86 |
| 7 | PO | 1 | 100 | 200 | 204 ± 142 |
| 8 | PO | 1 | 100 | 200 | 705 ± 118 |
| 8 | PO | 1 | 100 | 200 | 55 ± 51 |
| 9 | PO | 1 | 100 | 200 | 668 ± 103 |
| 10 | PO | 1 | 100 | 200 | 704 ± 80 |
| 10 | PO | 1 | 100 | 200 | 454 ± 680 |
| 11 | PO | 1 | 100 | 200 | 76 ± 65 |
| 12 | PO | 1 | 100 | 200 | 65 ± 146 |

Interferon—Oral Delivery

Dosing solutions of delivery agent compound and human interferon (IFN) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted to about 7.0 to 8.5. The delivery agent compound solution was mixed with an IFN stock solution (about 22.0 to 27.5 mg/ml in phosphate buffered saline) and diluting to the desired volume (usually 3.0 ml). The final delivery agent compound and IFN doses, and the dose volumes are listed below in Table 5.

The typical dosing and sampling protocols were as follows. Male Sprague-Dawley rats weighing between 200–250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 15, 30, 45, 60 and 90 minutes. Serum IFN concentrations were quantified using Cytoscreen Immunoassay Kit for human IFN-alpha (catalog # KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 5.

TABLE 5

Interferon - Oral Delivery

| Delivery Agent Compound | Delivery Agent Compound Dose (mg/kg) | IFN Dose (mg/kg) | Volume dose (ml/kg) | Mean Peak Serum [IFN] (ng/ml) ± SD |
|---|---|---|---|---|
| 1 | 200 | 1 | 1 | 1.8 ± 1.2 |
| 1 | 400 | 1 | 1 | 0.32 ± 0.46 |

EXAMPLE 6

Insulin—Oral Delivery

Oral dosing (PO) compositions of delivery agent compound and human zinc insulin (minimum 26 IU/mg available from Calbiochem—Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 1ON NaOH and 50 ml iN NaOH) was added to the solution and mixed by inverting. The solution may be used in the dosing protocol immediately, or alternatively, the solution may be placed into a 37° C. water bath for one hour prior to dosing. The final delivery agent compound dose, insulin dose and dose volume amounts are listed below in Table 6.

The typical dosing and sampling protocols were as follows. Male Sprague-Dawley rats weighing between about 200–250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with-a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations ($\mu$U/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) and the area under the curve (AUC) are reported below in Table 6.

Table 6. Insulin—Oral Delivery

| Delivery Agent Compound | Delivery Agent Compound Dose (mg/kg) | Insulin Dose (mg/kg) | Volume dose (ml/kg) | Mean Peak Serum [INS] ± SD |
|---|---|---|---|---|
| 1 | 100 | 3 | 1 | 100 ± 128 |
| 1 | 100 | 3 | 0.5 | 46 ± 55 |
| 1 | 100 | 3 | 0.5 | 8 ± 5 |
| 1 | 100 | 3 | 0.5 | 854 ± 1219 |
| 1 | 100 | 3 | 0.5 | 71 ± 128 |
| 1 | 100 | 3 | 0.5 | 262 ± 231 |
| 1 | 100 | 3 | 0.5 | 117 ± 208 |
| 1 | 100 | 2 | 0.5 | 95 ± 97 |
| 1 | 100 | 1 | 0.5 | 18 ± 9 |
| 1 | 100 | 0.5 | 0.5 | 30 ± 56 |
| 1 | 100 | 0.25 | 0.5 | 54 ± 84 |
| 1 | 200 | 3 | 1 | 1941 ± 1337 |
| 1 | 100 | 3 | 1 | 139 ± 114 |
| 1 | 100 | 3 | 0.5 | 632 ± 1213 |
| 1 | 200 | 3 | 1 | 1983 ± 1926 |
| 1 | 100 | 3 | 1 | 340 ± 84 |
| 1 | 100 | 3 | 0.5 | 644 ± 728 |
| 1 | 200 | 0.5 | 1 | 65 ± 76 |
| 1 | 200 | 3 | 1 | 1590 ± 338 |

The above mentioned patents, applications, test methods, publications are hereby incorporated by reference their entirety.

Many variations of the present invention will suggest themselves to those skilled in the art in light of the above detailed description. All such obvious variations are within the fully intended scope of the appended claims.

What is claimed is:

1. A compound selected from the group consisting of compounds:

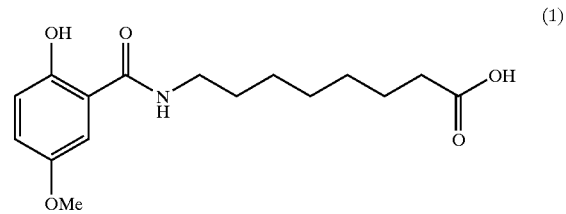

(1)

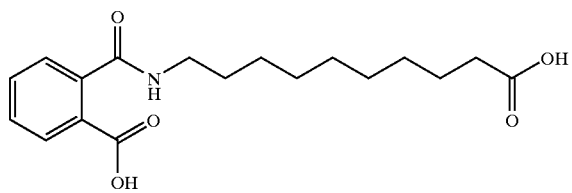

(2)

and salts thereof.

2. A composition comprising:

(A) an active agent; and (B) the compound of claim 1, and mixtures thereof.

3. The composition of claim 2, wherein the active agent is selected from the group consisting of a biologically active agent, a chemically active agent, and a combination thereof.

4. The composition of claim 3, wherein the biologically active agent comprises at least one protein, polypeptide, peptide, hormome, polysaccharide, mucopolysaccharide, carbohydrate, or lipid.

5. The composition of claim 3, wherein the biologically active agent is selected from the group consisting of: growth hormones, human growth hormones recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor (IGF), IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin; erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim. postaglandins, cyclosporin, vasopressin, cromolym sodium, sodium chromoglycate, disodium chromoglycate, vancomycin, desferrioxamine (DFO), parathyroid hormone (PTH), fragments of PTH, antimicrobials, anti-fungal agents, vitamins; analogs, fragments, mimetics and polyethylene glycol (PEG)-modified derivatives of these compounds; and any combination thereof.

6. The composition of claim 3, wherein the biologically active agent comprises insulin, heparin, calcitonin, parathyroid hormone, erythropoietin, growth hormones or combinations thereof.

7. The composition of claim 3, wherein the biologically active agent comprises recombinant human growth hormones.

8. The composition of claim 3, wherein the biologically active agent comprises parathyroid hormone.

9. The composition of claim 3, wherein the biologically active agent comprises insulin.

10. The composition of claim 3, wherein the biologically active agent comprises heparin.

11. The composition of claim 3, wherein the biologically active agent comprises calcitonin.

12. The composition of claim 3, wherein the biologically active agent comprises interferon.

13. A composition comprising:
(A) an active agent; and
(B) a poly(amino acid) comprising a compound having a formula selected from the group consisting of the compounds of claim 1, salts thereof and mixtures thereof.

14. The composition of claim 13 wherein the poly (amino acid) is a polypeptide.

15. A dosage unit form comprising:
(A) the composition of claim 2; and
(B) (a) an excipient
   (b) a dilutent
   (c) a disintegrant,
   (d) a lubricant,
   (e) a plasticizer,
   (f) a colorant,
   (g) a dosing vehicle, or
   (h) any combination thereof.

16. The dosage unit form of claim 15, wherein the active agent is selected from the group consisting of a biologically active agent, a chemically active agent, and a combination thereof.

17. The dosage unit form of claim 16, wherein the biologically active agent comprises at least one protein, polypeptide, peptide, hormone, polysaccharide, mucopolysaccharide, carbohydrate, or lipid.

18. The dosage unit form of claim 16, wherein the biologically active agent is selected from the group consisting of:

growth hormones, human growth hormones (hGH), recombinant human growth hormones (rhGH), bovine growth hormones, porcine growth hormones, growth hormone releasing hormones, growth hormone releasing factor, interferons, α-interferon, β-interferon, γ-interferon, interleukin-1, interleukin-2, insulin, porcine insulin, bovine insulin, human insulin, human recombinant insulin, insulin-like growth factor, insulin-like growth factor-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin;

erythropoietin, atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoeitin, filgrastim, postaglandins, cyclosporin, vasopressin, cromolym sodium, sodium chromoglycate, disodium chromoglycate, vancomycin, desferrioxamine, parathyroid hormone, fragments of PTH, antimicrobials, anti-fungal agents, vitamins; analogs, fragments, mimetics and polyethylene glycol-modified derivatives of these compounds; and any combination thereof.

19. The dosage unit form of claim 16, wherein the biologically active agent comprises insulin, heparin, calcitonin, parathyroid hormone, erythropoietin, human growth hormones or combinations thereof.

20. The dosage unit form of claim 15, wherein the active agent comprises recombinant human growth hormone.

21. The dosage unit form of claim 15, wherein the active agent comprises parathyroid hormone.

22. The dosage unit form of claim 15, wherein the active agent comprises insulin.

23. The dosage unit form of claim 15, wherein the active agent comprises heparin.

24. The dosage unit form of claim 15, wherein the active agent comprises calcitonin.

25. The dosage unit form of claim 15, wherein the active agent comprises interferon.

26. The dosage unit form of claim 15, wherein the dosage unit form comprises a dosing vehicle comprising a tablet, a capsule, a powder, or a liquid.

27. The dosage unit form of claim 15, wherein the dosing vehicle is liquid selected from the group consisting or water, 1,2-propane diol, ethanol, and any combination.

28. A method for administering a biologically-active agent to an animal in need of the agent, the method comprising administering orally to the animal the composition of claim 3.

29. A method for preparing a composition comprising mixing:
(A) at least one active agent;
(B) the compound of claim 1; and
(C) optionally, a dosing vehicle.

* * * * *

UNITED STATES PATENT AND TRADEMARK OFFICE
CERTIFICATE OF CORRECTION

PATENT NO.      : 6,693,208 B2
DATED           : February 17, 2004
INVENTOR(S)     : David Gschneidner et al.

It is certified that error appears in the above-identified patent and that said Letters Patent is hereby corrected as shown below:

<u>Title page,</u>
Item [22], PCT filing date,
In the PCT § 371 ©(1), (2), (4) Date:
Delete "July 16, 2002" and substitute -- July 15, 2002 --.

Signed and Sealed this

First Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO.     : 6,693,208 B2
DATED          : February 17, 2004
INVENTOR(S)    : David Gschneidner et al.

It is certified that error appears in the above-identified patent and that said Letters Patent is hereby corrected as shown below:

<u>Title page</u>,
Item [75], Inventors, please delete "David Gscheidner" and substitute -- David Gschneidner --.

Signed and Sealed this

Fourteenth Day of September, 2004

JON W. DUDAS
*Director of the United States Patent and Trademark Office*